(12) United States Patent
Higgins et al.

(10) Patent No.: US 9,486,445 B2
(45) Date of Patent: Nov. 8, 2016

(54) COMBINATION THERAPY FOR PROLIFERATIVE DISORDERS

(71) Applicant: Hoffmann-La Roche Inc., Nutley, NJ (US)

(72) Inventors: Brian Higgins, Fresh Meadows, NY (US); Kenneth Kolinsky, Bloomingdale, NJ (US); Gwen Nichols, New York, NY (US); Kathryn Packman, Bloomfield, NJ (US); Fei Su, Paramus, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/806,427

(22) Filed: Jul. 22, 2015

(65) Prior Publication Data

US 2016/0051525 A1    Feb. 25, 2016

Related U.S. Application Data

(63) Continuation of application No. 13/759,458, filed on Feb. 5, 2013, now Pat. No. 9,216,170.

(60) Provisional application No. 61/612,441, filed on Mar. 19, 2012.

(51) Int. Cl.
*A61K 31/437* (2006.01)
*A61K 31/496* (2006.01)
*A61K 31/40* (2006.01)

(52) U.S. Cl.
CPC ............. *A61K 31/437* (2013.01); *A61K 31/40* (2013.01); *A61K 31/496* (2013.01)

(58) Field of Classification Search
CPC .................................................. A61K 31/437
USPC .................................................... 514/254.05
See application file for complete search history.

(56) References Cited

U.S. PATENT DOCUMENTS

| 7,504,509 | B2 | 3/2009 | Ibrahim et al. |
| 7,851,626 | B2 | 12/2010 | Ding et al. |
| 7,863,288 | B2 | 1/2011 | Ibrahim et al. |
| 8,143,271 | B2 | 3/2012 | Ibrahim et al. |
| 8,329,724 | B2 | 12/2012 | Hildbrand et al. |
| 8,470,818 | B2 | 6/2013 | Ibrahim et al. |
| 8,530,661 | B2 | 9/2013 | Hildbrand et al. |
| 2010/0152190 | A1 | 6/2010 | Bartkovitz et al. |
| 2010/0310659 | A1 | 12/2010 | Desai et al. |
| 2011/0112136 | A1 | 5/2011 | Diodone et al. |
| 2012/0022258 | A1 | 1/2012 | Brumsted et al. |
| 2012/0045433 | A1 | 2/2012 | Dhingra et al. |
| 2012/0045434 | A1 | 2/2012 | Dhingra et al. |
| 2012/0148533 | A1 | 6/2012 | Dhingra et al. |
| 2012/0214828 | A1 | 8/2012 | Hatzivassiliou et al. |
| 2013/0172375 | A1 | 7/2013 | Albano et al. |
| 2013/0245039 | A1 | 9/2013 | Higgins et al. |

FOREIGN PATENT DOCUMENTS

| WO | WO 2011/098398 | 8/2011 |
| WO | WO 2012/135750 | 10/2012 |
| WO | WO 2012/161776 | 11/2012 |
| WO | WO 2013/063001 | 5/2013 |

OTHER PUBLICATIONS

Canal et al. "Benefits of Pharmacological Knowledge in the Design and Monitoring of Cancer Chemotherapy," *Pathol. Oncol. Res.* 4(3):171-178, (1998).
Kim et al., "The HSP90 Inhibitor XL888 Overcomes BRAF Inhibitor Resistance Mediated through Diverse Mechanisms," *Clin. Cancer Res.* 18:2502-2512 (2012).
Lee et al., "MEK'ing the Most of p53 Reactivation Therapy in Melanoma," *J. Invest. Dermatol.* 132:263-265 (2012).
Shi et al., "Combinatorial Treatments that Overcome PDGFRβ-Driven Resistance of Melanoma Cells to V600EB-RAF Inhibition," *Cancer Res.* 71:5067-5074 (2011).
Yang et al., "RG7204 (PLX4032), a Selective BRAFV600E Inhibitor, Displays Potent Antitumor Activity in Preclinical Melanoma Models," *Cancer Res.* 70:5518-5527 (2010).

*Primary Examiner* — Andrew D Kosar
*Assistant Examiner* — Taofiq A Solola
(74) *Attorney, Agent, or Firm* — Morrison & Foerster LLP

(57) ABSTRACT

Treatment of proliferative diseases with a combination of a b-Raf inhibitor and MDM2 inhibitor.

15 Claims, 1 Drawing Sheet

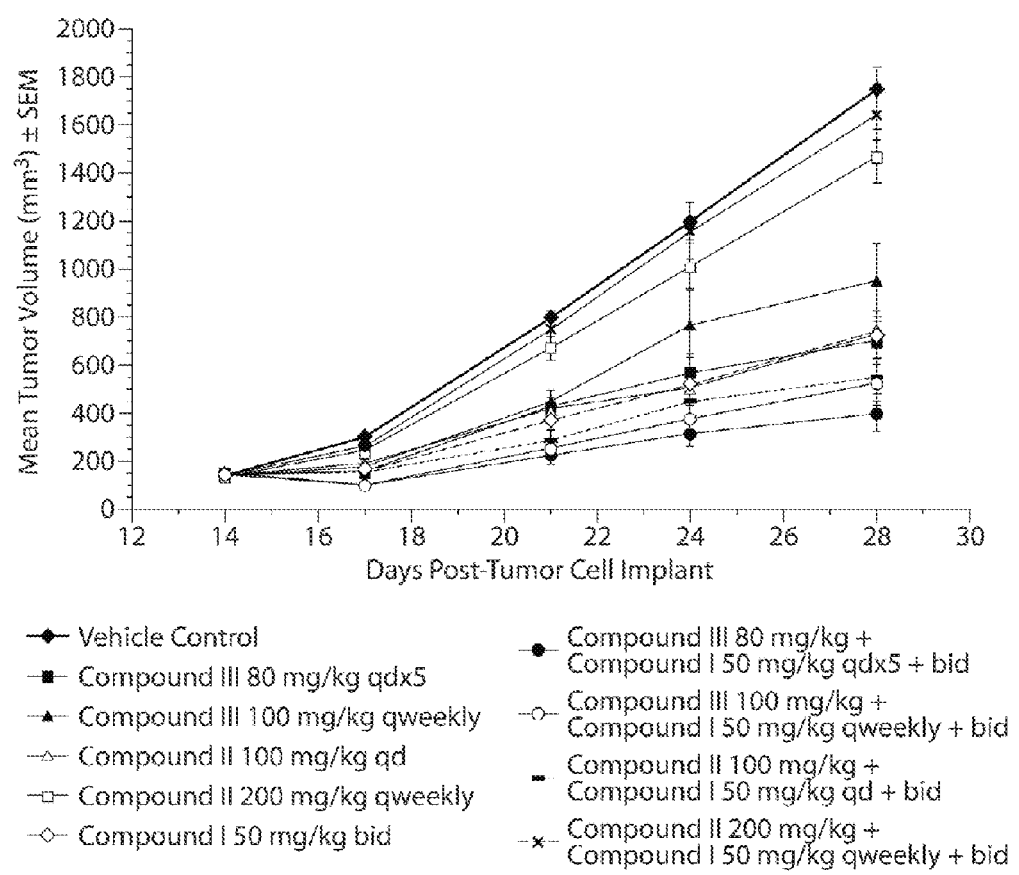

COMBINATION THERAPY FOR PROLIFERATIVE DISORDERS

PRIORITY TO RELATED APPLICATION(S)

This application is a continuation of U.S. patent application Ser. No. 13/759,458, filed Feb. 5, 2013, which claims the benefit of U.S. Provisional Application No. 61/612,441, filed Mar. 19, 2012, the contents of which are hereby incorporated by reference in their entireties.

FIELD OF THE INVENTION

The present invention relates to a combination therapy for treating a patient suffering from a proliferative disorder, in particular a solid tumor, for example, colorectal cancer, melanoma, sarcoma and thyroid cancer, comprising administering to the patient concomitantly or sequentially, (i) the b-Raf inhibitor vemurafenib and (ii) a MDM2 inhibitor.

BACKGROUND OF THE INVENTION

Vemurafenib (sometimes referred to as Compound I) is a b-raf kinase inhibitor that specifically targets mutant b-Raf having the V600E mutation. Vemurafenib is commercially available as Zelboraf™, Genentech, South San Francisco, Calif. This compound is described in U.S. Pat. Nos. 7,504,509 and 7,863,288. Vemurafenib is currently approved for the treatment of V600E mutation positive metastatic melanoma and is undergoing investigation for the inhibition of several other tumors, for example, colorectal and thyroid cancers.

p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells.

The ratio of MDM2 to p53 is dysregulated in many cancers. Activation of p53 by antagonizing its negative regulator MDM2 is thus a useful strategy in treating cancer and several MDM2 antagonists are in development. For example, (4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3-(methylsulfonyl)propyl]-piperazine (referred to herein as Compound II) and 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (referred to herein as Compound III) are in phase I clinical trials for the treatment of solid tumors. Compound II is disclosed in U.S. Pat. No. 7,851,626. Compound III is disclosed in US Pub 2010/0152190 A1. To the extent deemed necessary, both of these publications are herein incorporated by reference.

Applicants have unexpectedly found that combination therapy with vemurafenib and an MDM2 inhibitor not only is capable of overcoming resistance to vemurafenib (that is, potentiation of activity in previously vemurafenib resistant cells), but also results in improved antineoplastic effects that are significantly superior to the results obtained with each compound alone, without a significant increase in toxicity. Moreover, because these two types of compounds exert antitumor effects by affecting different cellular mechanisms, a therapeutic combination of both compounds is expected to yield improved antitumor activity in certain tumors and/or prevent or delay resistance to drug therapy.

SUMMARY OF THE INVENTION

The present invention relates to a method of treating a patient suffering from a proliferative disorder, in particular cancer, comprising administering to the patient, either concomitantly or sequentially, (i) a first component comprising, as an active agent, vemurafenib, or a pharmaceutically-acceptable salt thereof, and (ii) a second component comprising, as an active agent, an MDM2 inhibitor, the amount of said active agents being such that the combination thereof is therapeutically-effective in the treatment of said proliferative disorder.

The invention also relates to a kit comprising (i) first component comprising, as an active agent, one or more oral unit dosage forms of vemurafenib; and (ii) a second component comprising, as an active agent, one or more oral or injectable unit dosage forms of an MDM2 inhibitor.

The present invention further relates to a pharmaceutical composition comprising a therapeutically effective amount of (i) vemurafenib, or a pharmaceutically-acceptable salt thereof, and (ii) an MDM2 inhibitor.

In addition, the present invention relates to the use vemurafenib, or a pharmaceutically-acceptable salt thereof, and an MDM2 inhibitor for the treatment of a proliferative disorder.

A yet further aspect of the present invention is the use of vemurafenib, or a pharmaceutically-acceptable salt thereof, and an MDM2 inhibitor for the preparation of a medicament for the treatment of a proliferative disorder.

BRIEF DESCRIPTION OF THE DRAWINGS

FIG. 1 illustrates the antitumor activity, as demonstrated by the change in mean tumor volume over time, of vemurafenib monotherapy, Compound II and Compound III monotherapy, and vemurafenib plus Compound II and vemurafenib plus Compound III combination therapy.

DETAILED DESCRIPTION OF THE INVENTION

As used herein, the terms "antineoplastic" or "antitumor" mean inhibiting the development, maturation or proliferation of malignant cells.

As used herein, the terms "cancer" and "cancerous" refer to or describe the physiological condition in mammals that is typically characterized by unregulated cell growth/proliferation. Examples of cancer include, but are not limited to, solid cancers such colorectal cancer, melanoma, thyroid cancer, or blood cancer (leukemia).

The term "colorectal tumor" or "colorectal cancer" refers to any tumor or cancer of the large bowel, which includes the colon (the large intestine from the cecum to the rectum) and the rectum, including, e.g., adenocarcinomas and less prevalent forms, such as lymphomas and squamous cell carcinomas.

As used herein Compound II refers to (4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3-(methylsulfonyl)propyl]-piperazine, which has the structure shown below in formula II,

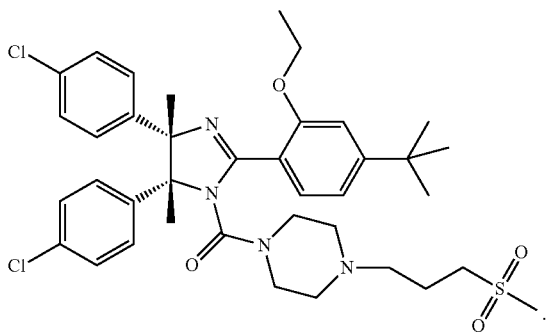

As used herein "Compound III" refers to 4-{[2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, which has the structure shown below in formula III,

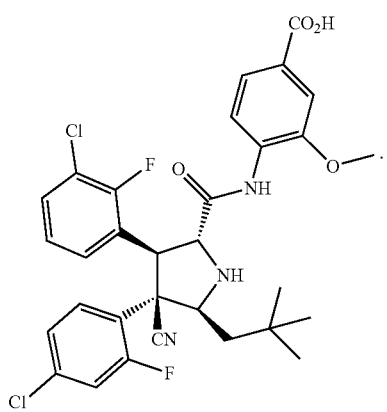

As used herein, the term "concomitant" means administration of both components during the same 24 hour period, preferably within one or two hours of each other, most preferably within about one half hour of each other.

"Inhibiting cell growth or proliferation" means decreasing a cell's growth or proliferation by at least 10%, 20%, 30%, 40%, 50%, 60%, 70%, 80%, 90%, 95%, or 100%, and includes inducing cell death.

As used herein, an "MDM2 inhibitor" is a compound that wholly or partly interferes with MDM2 binding to p53.

As used herein, the term "pharmaceutically acceptable salt" of a compound refers to any conventional salt or base addition salt that retains the biological effectiveness and properties of the compound and which is formed from a suitable organic or inorganic acid or organic or inorganic base.

"Regression" of a tumor is said to occur following treatment when the volume of said tumor is reduced. If the tumor remains present (tumor volume>0 $mm^3$) but its volume is reduced from what it was at the initiation of treatment, "partial regression" (PR) is said to have occurred. If the tumor is palpably absent following treatment, "complete regression" (CR) is said to have occurred.

As used herein, the terms "sequential administration" or "administered sequentially" means that one component is administered more than twenty four hours after the other component, preferably within 2-15 days of the other component.

As used herein, the term "therapeutically effective" means an amount of drug, or combination or composition, which is effective for producing a desired therapeutic effect upon administration to a patient, for example, to stem the growth, or result in the shrinkage, of a cancerous tumor or to increase the patient's life span.

"Therapeutic index" is a well-recognized term of art and is an important parameter in the selection of anticancer agents for clinical trial. Therapeutic Index takes into consideration the efficacy, pharmacokinetics, metabolism and bioavailability of anticancer agents. See, e.g., J. Natl. Cancer Inst. 81(13): 988-94 (Jul. 5, 1989).

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

As sated above, "vemurafenib" is a b-Raf kinase inhibitor that specifically targets b-Raf having the V600E mutation. Its chemical structure and name are as follows:

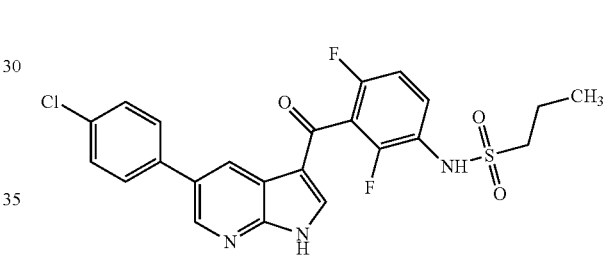

Propane-1-sulfonic acid {3-[5-(4-chlorophenyl)-1H-pyrrolo[2,3-b]pyridine-3-carbonyl-2,4-difluoro-phenyl]-amide} (Compound I).

The "V600E" mutation of b-Raf, as used herein, refers to a mutation in the b-Raf protein wherein the valine residue at residue position 600 of b-Raf is replaced by glutamic acid.

In one aspect, the present invention relates to a method of treating a patient suffering from a proliferative disorder, comprising administering to the patient, either concomitantly or sequentially, (i) a first component comprising, as an active agent, vemurafenib, or a pharmaceutically-acceptable salt thereof, and (ii) a second component comprising, as an active agent, an MDM2 inhibitor, the amount of said active agents being such that the combination thereof is therapeutically-effective in the treatment of said proliferative disorder.

Treatment of a proliferative disorder shall be understood to include maintaining or decreasing tumor size, inducing tumor regression (either partial or complete), inhibiting tumor growth, and/or increasing the life span of a patient suffering from said disorder.

The present invention also relates to a kit comprising (i) a first component comprising, as an active agent, one or more oral unit dosage forms of vemurafenib, or a pharmaceutically acceptable salt thereof; and (ii) a second component comprising, as an active agent, one or more oral or injectable unit dosage forms of an MDM2 inhibitor, or a pharmaceutically acceptable salt thereof.

The kit or composition may be used, for example, in the treatment of a proliferative disorder.

In an embodiment of the invention, the proliferative disorder is a solid tumor. Such tumors include, for example, colorectal cancer, melanoma, sarcoma and thyroid cancer.

In another embodiment the proliferative disorder is leukemia.

In yet a further embodiment of the invention, the proliferative disorder is a solid tumor comprising b-Raf having the V600E mutation.

In another embodiment of the invention, the proliferative disorder is a tumor comprising b-Raf having the V600E mutation.

In a further embodiment of the invention, the proliferative disorder is selected from the group consisting of colorectal cancer, melanoma, and thyroid cancer and the cancer involves a tumor comprising b-Raf having the V600E mutation.

In yet a further embodiment of the invention, the proliferative disorder is colorectal cancer.

In yet a further embodiment of the invention, the proliferative disorder is colorectal cancer involving a tumor comprising b-Raf having the V600E mutation.

In yet a further embodiment of the invention, the MDM2 inhibitor is a small molecule MDM2 inhibitor. In one such embodiment, the MDM2 inhibitor is selected from Compound I or Compound II.

In yet a further embodiment of the invention, the present invention relates to a method of treating a patient suffering from colorectal cancer involving a tumor comprising b-Raf having the V600E mutation, wherein said method comprises administering to the patient, either concomitantly or sequentially, (i) a first component comprising, as an active agent, vemurafenib, or a pharmaceutically-acceptable salt, and (ii) a second component comprising, as an active agent, Compound II, or a pharmaceutically acceptable salt thereof, the amount of said active agents being such that the combination thereof is therapeutically-effective in the treatment of said cancer.

In yet a further embodiment of the invention, the present invention relates to a method of treating a patient suffering from colorectal cancer involving a tumor comprising b-Raf having the V600E mutation, wherein said method comprises administering to the patient, either concomitantly or sequentially, (i) a first component comprising, as an active agent, vemurafenib, or a pharmaceutically-acceptable salt thereof, and (ii) a second component comprising, as an active agent, Compound III, or a pharmaceutically acceptable salt thereof, the amount of said active agents being such that the combination thereof is therapeutically-effective in the treatment of said cancer.

The amount of each component administered according to the present method may, but does not have to be therapeutically effective by itself. That is, this invention specifically contemplates combinations wherein the amount of vemurafenib, or a pharmaceutically-acceptable salt thereof, and/or the amount of MDM2 inhibitor in the combination may be less than the amount judged therapeutically-effective for each active agent when said agent is administered in monotherapy.

Vemurafenib, or a pharmaceutically-acceptable salt, may, for example, be administered orally. Compounds I and II may be administered orally or by injection.

The first component and the second component of the present invention are administered in any amount and for any duration that the combined amounts thereof are therapeutically effective in treating a proliferative disorder.

In the context of this application, the dosages refer to the amount of vemurafenib or MDM2 inhibitor. Thus, when a salt of either component is contemplated, the amount of the salt would be adjusted such as to deliver to the patient the recited dose of the vemurafenib or MDM2 inhibitor.

In embodiments of the present invention, vemurafenib, or a pharmaceutically acceptable salt thereof, is administered at a dosage amount of from about 200 mg/day to about 3000 mg/day, from about 300 mg/day to about 2000 mg/day, from about 960 mg/day to about 2000 mg/day, or from about 960 mg/day to about 1920 mg/day. In yet another embodiment, the dosage amount is about 500 mg/day. In yet another embodiment, the dosage amount is about 1820 mg/day.

In an embodiment of the present invention, the foregoing amounts of vemurafenib, or a pharmaceutically acceptable salt, may be administered as a single dose daily or divided, for example into equal doses (though this is not required), and administered twice daily (bid). For example, vemurafenib, or a pharmaceutically acceptable salt thereof, may be administered in a dosage amount of from about 100 mg to about 1500 mg bid, from about 150 mg to about 1000 mg bid, from about 480 mg to about 1000 mg bid, from about 480 mg to about 960 mg bid, or about 960 mg bid.

In embodiments of the present invention, Compound II, or a pharmaceutically acceptable salt thereof, is administered at a dosage amount of from about 100 mg/day to about 4500 mg/day, from about 500 mg/day to about 3500 mg/day, or from about 2000 mg/day to about 3000 mg/day. In an embodiment, Compound II is administered in at a dosage amount of about 2500 mg/day. In another embodiment, Compound II is administered at a dosage amount of about 3000 mg/day. In another embodiment, Compound II is administered at a dosage amount of about 3,500 mg/day. Compound II may be administered as a single dose daily or divided into multiple daily doses.

In embodiments of the present invention, Compound III, or a pharmaceutically acceptable salt thereof, is administered at a dosage amount of from about 100 mg/day to about 2500 mg/day, from about 300 mg/day to about 2000 mg/day, or from about 800 mg/day to about 1800 mg/day. In an embodiment, Compound III is administered at a dosage amount of about 2500 mg/day. In another embodiment, Compound III is administered at a dosage amount of about 1500 mg/day. Compound III may be administered as a single dose daily or divided into multiple daily doses.

The present invention further provides a method for treating a proliferative disorder wherein vemurafenib, or a pharmaceutically-acceptable salt thereof, is administered in a dosage amount of from about 200 mg/day to about 3000 mg/day, particularly in a dosage amount of from about 960 mg/day to about 2000 mg/day and Compound II, or a pharmaceutically acceptable salt thereof, is administered in a dosage amount of from about 500 mg/day to about 3500 mg/day. In an embodiment of this invention, the proliferative disorder treated according to this method is a solid tumor, in particular the disorder is selected from the group consisting of colorectal cancer, melanoma, and thyroid cancer. In another embodiment of this invention, the proliferative disorder involves a tumor comprising b-Raf having the V600E mutation. In a particular embodiment of this invention, the proliferative disorder is colorectal cancer involving a tumor comprising b-Raf having the V600E mutation.

The present invention further provides a method for treating a proliferative disorder wherein vemurafenib, or a pharmaceutically-acceptable salt thereof, is administered in a dosage amount of from about 200 mg/day to about 3000 mg/day, particularly in a dosage amount of from about 960 mg/day to about 2000 mg/day, and Compound III, or a pharmaceutically acceptable salt thereof, is administered in a dosage amount of from about 300 mg/day to about 2000 mg/day, particularly in a dosage amount of from about 800 mg/day to about 1800 mg/day.

In an embodiment of this invention, the proliferative disorder treated with this method is a solid tumor, in particular the disorder is selected from the group consisting of colorectal cancer, melanoma, sarcoma and thyroid cancer. In another embodiment, the proliferative disorder is leukemia. In another embodiment of this invention, the proliferative disorder involves a tumor comprising b-Raf having the V600E mutation. In a particular embodiment of this invention, the proliferative disorder is colorectal cancer involving a tumor comprising b-Raf having the V600E mutation.

The present invention provides a method of treating a patient suffering from a proliferative disorder, comprising administering to the patient: (i) a first component comprising, as an active agent, vemurafenib, or a pharmaceutically-acceptable salt thereof, in an amount of from about 200 mg/day to about 3000 mg/day; and (ii) a second component comprising, as an active agent, (4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3-(methylsulfonyl)propyl]-piperazine (Compound II), or a pharmaceutically acceptable salt thereof, in an amount of from about 100 mg/day to about 4500 mg/day, more particularly from about 500 mg/day to about 3500 mg/day. More specifically, vemurafenib, or a pharmaceutically-acceptable salt thereof, is administered in an amount from about 960 mg/day to about 1920 mg/day and Compound II is administered in an amount of from about 500 mg/day to about 3500 mg/day.

The present invention also provides a method of treating a patient suffering from a proliferative disorder, comprising administering to the patient: (I) a first component which comprises, as an active agent, vemurafenib, or a pharmaceutically-acceptable salt thereof, in an amount of from about 200 mg/day to about 3000 mg/day; and (ii) a second component which comprises, as an active agent, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (Compound III), or a pharmaceutically acceptable salt thereof, is administered in an amount of from about 300 mg/day to about 2000 mg/day, more particularly from about 800 mg/day to about 1800 mg/day. More specifically, vemurafenib, or a pharmaceutically-acceptable salt thereof, is administered in an amount from about 960 mg/day to about 1920 mg/day and Compound III is administered in an amount from about 800 to about 1800 mg/day.

The present invention also further provides a kit or a composition comprising: (i) a first component comprising, as an active agent, one or more unit dosage forms of vemurafenib, or a pharmaceutically-acceptable salt thereof; and (ii) a second component comprising, as an active agent, one or more unit dosage forms of (4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3-(methylsulfonyl)propyl]-piperazine, or a pharmaceutically acceptable salt thereof.

The present invention also further provides a kit or a composition comprising: (i) a first component comprising, as an active agent, one or more unit dosage forms of vemurafenib, or a pharmaceutically-acceptable salt thereof; and (ii) a second component comprising, as an active agent, one or more unit dosage forms of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, or a pharmaceutically acceptable salt thereof.

In another aspect of this invention, the components herein described above are administered together with radiotherapy and/or together with another active agent.

As previously stated, the amount of each component administered according to the present method may, but does not have to be therapeutically effective by itself and this invention specifically contemplates combinations wherein the amount of each of the active agents in the combination may be less than the amount judged therapeutically-effective for each active agent when said agent is administered in monotherapy.

The two components of the invention, that is a pharmaceutical composition containing vemurafenib and a pharmaceutical composition containing an MDM2 inhibitor, may be administered concomitantly or sequentially over such period of time so as to obtain maximum therapeutic effect. As is demonstrated below, when the components are administered sequentially, either component may be administered first. In a preferred embodiment, both components are administered concomitantly.

In accordance with the present invention, administration of the two components, concomitantly or sequentially, enhances the treatment of cancer as compared to administering each component independently in monotherapy. For example, the amount of the MDM2 inhibitor required in the combination therapy is expected to be less than the amount needed in monotherapy. Thus, the combination effect results in an improved therapeutic index as compared to either agent alone while toxicity remains acceptable.

Preferably, both components are administered to the patient in an oral unit dosage form, more preferably in capsule or tablet form.

The dosage levels of each of the components may be modified by the physician to be lower or higher than that stated herein depending on the needs of the patient, and the reaction of the patient to the treatment. The dosages may be administered according to any dosage schedule determined by the physician in accordance with the requirements of the patient. For example, the dosages of each of the components may be administered in single or in divided doses over a period of several days, or alternating daily schedules.

In an embodiment, administration of the composition containing vemurafenib and the composition containing Compound II occur on the first day of a 28 day cycle (that is a 4 week repeating cycle). The composition containing vemurafenib is administered twice daily approximately 12 hours apart and is administered continuously until disease progression or unacceptable toxicity occurs. The composition containing Compound II is administered once daily for up to about 5 days on days 1-5 of a 28 day cycle. Alternatively, the composition containing Compound II is administered daily for up to about 10 days on days 1-10 of a 28 day cycle. Alternatively, the composition containing Compound II is administered once daily on days 1, 8 and 15 of a 28 day cycle. Each cycle is then repeated for a total of up to about 16-24 doses.

In an embodiment, administration of the composition containing vemurafenib and the composition containing Compound III occur on the first day of a 28 day cycle (4 week repeating cycle). The composition containing vemurafenib is administered twice daily approximately 12 hours apart and is administered continuously until disease progression or unacceptable toxicity occurs. The composition containing Compound III is administered once daily for up to about 5 days on days 1-5 of a 28 day cycle. Alternatively, the composition containing Compound III is administered daily for up to about 10 days on days 1-10 of a 28 day cycle. Alternatively, the composition containing Compound III is administered once daily on days 1, 8 and 15 of a 28 day cycle. Each cycle is then repeated for a total of up to about 16-24 doses.

In an embodiment, vemurafenib, or a pharmaceutically-acceptable salt thereof is administered in an amount from about 480 mg to about 960 mg bid daily on about day 1 through about day 28 of a 28 day cycle and Compound II is administered once daily in an amount of about 3500 mg/day, for up to about 5 days on days 1-5 of a 28 day cycle. Alternatively, Compound II is administered in an amount of about 1500 mg twice daily (BID) for up to 10 days on days 1-10 of a 28 day cycle. Alternatively, Compound II is administered once weekly in an amount from about 3000 mg/day to about 4500 mg/day, specifically 4500 mg/day, on days 1, 8 and 15 of a 28 day cycle.

In an embodiment, vemurafenib, or a pharmaceutically-acceptable salt thereof is administered in an amount from about 480 mg to about 960 mg bid daily on about day 1 through about day 28 of a 28 day cycle and Compound III is administered once daily in an amount from 300 mg/day to about 2000 mg/day for about for up to about 5 days on days 1-5 of a 28 day cycle.

Alternatively, Compound III is administered once weekly in an amount from about to about 2500 mg/day on days 1, 8 and 15 of a 28 day cycle.

Each component may also contain additional agents such as preserving agents, solubilizing agents, stabilizing agents, wetting agents, emulsifying agents, sweetening agents, coloring agents, flavoring agents, salts for varying the osmotic pressure, buffers, coating agents and antioxidants.

In addition, the present invention provides the use of vemurafenib, or a pharmaceutically-acceptable salt thereof, and an MDM2 inhibitor for the treatment of a proliferative disorder.

The invention further provides the use of vemurafenib, or a pharmaceutically-acceptable salt thereof, and an MDM2 inhibitor for the preparation of a medicament for the treatment of a proliferative disorder.

Applicants have conducted studies using mice containing a de novo vemurafenib resistant MDM2 non-amplified/non-overexpressing RKO colorectal cancer model. This p53 wildtype colorectal cancer line expresses the B-raf V600E mutation and is therefore believed to be a model of a difficult to treat human colorectal cancer.

Applicants found that the combination of vemurafenib at 50 mg/kg bid and Compound II at 200 mg/kg qweekly to tumor-bearing mice produced tumor growth inhibition (TGI) and increased life span (ILS) results that were significantly better than correlative monotherapy results at [p<0.05].

These studies indicate that treating patients with a combination of vemurafenib and Compound II would be superior to treatment with either agent alone. Further, they indicate that combining the two agents allows for at least reduction in the dose of vemurafenib to obtain equivalent or better results.

Applicants also found that the combination of vemurafenib at 50 mg/kg bid and Compound III at 100 mg/kg weekly to tumor-bearing mice produced growth inhibition (TGI) and increased life span (ILS) results that were significantly better than correlative monotherapy results at p<0.05.

These studies indicate that treating patients with a combination of vemurafenib and Compound III would be superior to treatment with either agent alone. Further, they indicate that combining the two agents allows for at least reduction in the dose of vemurafenib to obtain equivalent or better results.

The invention will be more fully understood by reference to the following examples. They should not, however, be construed as limiting the scope of the invention.

EXAMPLES

The efficacy of the combinations of the present invention on solid tumors is demonstrated by the following experiments.

Abbreviations used herein are as follows:
q.s. as much as needed
× times
po orally
ip intraperitoneally
bid twice daily
wk week
qd once daily
q4d ×5 once every four days for a total of five doses
BWL body weight loss
SEM standard error of the mean In the examples below, weight loss was graphically represented as percent change in mean group body weight, using the formula: $((W-W_0)/W_0)\times 100$, where 'W' represents mean body weight of the treated group at a particular day, and '$W_0$' represents mean body weight of the same treated group at initiation of treatment. Maximum weight loss was also represented using the above formula, and indicated the maximum percent body weight loss that was observed at any time during the entire experiment for a particular group.

Example 1

This example describes the formation of a suspension comprising the test compounds. A. Suspension of vemurafenib A solid molecular complex comprising vemurafenib and hydroxypropyl methyl cellulose acetate succinate (HPMC-AS) was first formed.

Vemurafenib and HPMC-AS in a ratio of approximately 3:7, respectively, were dissolved in dimethylacetamide (DMA). The resulting solution was then added with stirring to very cold dilute hydrochloric acid resulting in the co-precipitation of vemurafenib and HPMC-AS as a solid molecular complex wherein vemurafenib was present in a nanoparticulate size range. The ratio of DMA to acid was in the range of 1:5 to 1:10.

The co-precipitate was then washed with water to remove DMA, filtered, dried to <2% moisture content and passed through a #30 mesh screen prior to evaluation. The resulting solid molecular complex was 30% by weight vemurafenib and 70% by weight HPMC.

The complex was then blended with colloidal silicon dioxide (available as Aerosil® 200 from Evonik Industries AG, Essen, Germany) such that, per 100 g of the blend, 97 g was the complex and 3 g was colloidal silicon dioxide.

An aqueous vehicle containing 2% hydroxypropylcellulose (available as Klucel® LF from Aqualon, Wilmington, Del., USA) and 1N HCl at Qs to pH4 for the purpose of pH adjustment was then prepared.

23.2 ml of the vehicle was equilibrated to room temperature and slowly transferred into 773.2 mg of the aforementioned blend. The resulting preparation was then slowly mixed until a homogenous suspension was obtained. The resulting suspension contained 9.375 mg/ml of vemurafenib.

The suspension was stored at 2-8° C. and protected from light. B. Suspension of Compound II in 2% hydroxylpropyl cellulose (Klucel), 0.2% Polysorbate 80 (Tween 80) with 0.09% methylparaben and 0.01% propylparaben in water. The compound may be milled prior to prepare the suspension or milled as suspension.

The contents of the final suspension are as follows.

| Component | Amount (mg/mL) |
|---|---|
| Compound II | 12.5 mg/mL or 25 mg/mL |
| Klucel LF | 20 |
| Tween 80 | 2 |
| Mehtylparaben | 0.9 |
| Propylparaben | 0.1 |
| Water for Injection | Qs to 1.0 mL |

This provided a suspension that was 12.5 or 25 mg/ml Compound II.

The vehicle solution or the compound suspension was stored at 2 to 8° C. C. Suspension of Compound III in the vehicle solution (same as for Compound II).

A solid molecular complex comprising compound III and hydroxypropyl methyl cellulose acetate succinate (HPMC-AS) was first formed.

Compound III and HPMC-AS in a ratio of approximately 3:7 or 1:1, respectively, were dissolved in dimethylacetamide (DMA). The resulting solution was then added with stirring to very cold dilute hydrochloric acid resulting in the co-precipitation of compound III and HPMC-AS as a solid molecular complex wherein compound III was present in a nanoparticulate size range. The ratio of DMA to acid was in the range of 1:5 to 1:10.

The co-precipitate was then washed with water to remove DMA, filtered, dried to <2% moisture content and passed through a #30 mesh screen prior to evaluation. The resulting solid molecular complex was 30% by weight compound III and 70% by weight HPMCAS or 50% compound III and 50% by weight HPMCAS.

The complex was then suspended in the vehicle solution which is an aqueous vehicle containing 2% hydroxypropylcellulose (available as Klucel® LF from Aqualon, Wilmington, Del., USA) and 0.2% polysorbate 80 with 0.09% methyl paraben and 0.01% propyl paraben. The resulting preparation was then slowly mixed until a homogenous suspension was obtained. The resulting suspension contained 10 or 12.5 mg/ml of compound III.

The suspension was stored at 2-8° C. and protected from light.

The contents of the final suspension are as follows.

| Component | Amount |
|---|---|
| Compound III | 10 mg/mL or 12.5 mg/mL |
| Klucel LF | 20 |
| Tween 80 | 2 |
| Methylparaben | 0.9 |
| Propylparaben | 0.1 |
| Water for Injection | Qs to 1.0 mL |

This provided a suspension that was 10 mg/mL or 12.5 mg/mL Compound III. The solution was stored at 2 to 8° C.

Example 2

In Vivo Assays
In Vivo Implantation:

Mice were implanted with RKO cell xenografts. The mice, cell line used, and implantation are described below.

Female athymic Crl:NU-Foxn1nu mice were used for efficacy testing (Charles River, Wilmington, Mass., USA). Mice were 10-12 weeks of age and weighed 23-25 grams. The health of the mice was assessed daily by observation and analysis of blood samples taken from sentinel animals on shared shelf racks. All animals were allowed to acclimate and recover from shipping-related stress for one week. Autoclaved water and irradiated food (5058-ms Pico Lab mouse chow, Purina Mills, Richmond, Ind., USA) were provided ad libitum, and the animals were kept in a 12 hour light and dark cycle. Cages, bedding and water bottles were autoclaved before use and changed weekly. All animal experiments were conducted in accordance with the Guide for the Care and Use of Laboratory Animals, local regulations, and protocols approved by the Roche Animal Care and Use Committee in our AAALAC accredited facility.

RKO cells (American Type Culture Collection, Rockville, Md.) were maintained in DMEM media+10% (v/v) heat-inactivated FBS+1% (v/v) 200 nM L-glutamine. Each mouse received $2\times10^6$ cells in a total volume of 0.2 ml. Cells were implanted subcutaneously in the right flank of each mouse using a 1 cc syringe and a 26 gauge needle.

RKO xenograft-containing mice were randomized into groups of 10 mice each according to tumor volume so that all groups had similar starting mean tumor volumes of about 145 $mm^3$.

Treatment of the mice began on day 14 post-cell implant and ended at day 28 post cell implant. 10 groups of mice were used. Each group was subjected to a different therapy as follows:

(1) mice receiving vehicle control; qd po+bid po
(2) mice receiving Compound III at 80 mg/kg qd po qd ×5;
(3) mice receiving Compound III at 100 mg/kg po qweekly ×2;
(4) mice receiving Compound II at 100 mg/kg po qd ×14;
(5) mice receiving Compound II at 200 mg/kg po qweekly ×2;
(6) mice receiving vemurafenib at 50 mg/kg po bid ×14;
(7) mice receiving Compound III 80 mg/kg qd ×5+vemurafenib 50 mg/kg bid
(8) mice receiving Compound III 100 mg/kg qweekly+vemurafenib 50 mg/kg bid
(9) mice receiving Compound II 100 mg/kg qd+vemurafenib 50 mg/kg bid
(10) mice receiving Compound II 200 mg/kg qweekly+vemurafenib 50 mg/kg bid Compounds were administered orally (po) using a 1 cc syringe and 18-gauge gavage needle (0.2 ml/animal). Concurrent dosing for combination groups was done in the morning with MDM2 inhibitor and vemurafenib being administered to each mouse in quick succession of each other separately and in no particular order. A second vemurafenib dose was given 8 hours later in the afternoon. Treatment duration was 2 weeks. All dosing was based on an average mouse weight of 25 grams.

Tumor volumes and animal body weights were measured two-three times per week and animals were monitored for clinical signs daily.

Toxicity

No toxicity was observed in the current study with any dose or schedule, monotherapy or combination. A technical death related to misdosing was observed, however this death was considered non-drug-related.

Weight loss was graphically represented as percent change in mean group body weight, using the formula: $((W-W_0)/W_0) \times 100$, where 'W' represents mean body weight of the treated group at a particular day, and 'W0' represents mean body weight of the same treated group at initiation of treatment. Maximum weight loss was also represented using the above formula, and indicated the maximum percent body weight loss that was observed at any time during the entire experiment for a particular group. Toxicity is defined as ≥20% of mice in a given group demonstrating ≥20% body weight loss and/or death.

The results of the experiment are shown in Table 1.

Tumor volume (in cubic millimeters) was calculated using the ellipsoid formula: $(D \times (d2))/2$ where 'D' represents the large diameter of the tumor, and 'd' represents the small diameter. In some cases, tumor regression and/or percent change in tumor volume was calculated using the formula: $((T-T_0)/T_0) \times 100$ where 'T' represents mean tumor volume of the treated group at a particular day, and '$T_0$' represents mean tumor volume of the same treated group at initiation of treatment.

Statistical analysis of treated groups was compared with the vehicle group with Mann-Whitney Rank Sum Test, comparisons between groups were analyzed by one-way ANOVA, and post-hoc Bonferroni t-test (GraphPad Prism, version 5.03). Differences between groups were considered to be significant when the probability value (p) was ≤0.05.

For survival assessment, results are plotted as the percentage survival against days after tumor implant (GraphPad

TABLE 1

Toxicity Summary

| Group | Frequency | Route | % Change in Body Weight at end of Study Day 28 | Max % Weight Loss | Max % Weight Gain | # of animals ≥20% BWL | Mortality | Reason for mortality/ morbidity |
|---|---|---|---|---|---|---|---|---|
| Vehicle control | qd + bid | po, po | 4.4 | 4.4 | 6.3 | 0 | 0 | N/A |
| Compound III 80 mg/kg | qdx5 | po | 5.3 | 5.3 | 7.4 | 0 | 0 | N/A |
| Compound III 100 mg/kg | qweekly | po | 6.6 | 4.7 | 7.5 | 0 | 0 | N/A |
| Compound II 100 mg/kg | qd | po | 8.4 | 5.0 | 10.0 | 0 | 1 | Technical |
| Compound II 200 mg/kg | qweekly | po | 5.2 | 3.7 | 7.8 | 0 | 0 | N/A |
| vemurafenib 50 mg/kg | bid | po | 4.6 | 2.8 | 7.5 | 0 | 0 | N/A |
| Compound III 80 mg/kg + vemurafenib 50 mg/kg | qdx5 + bid | po, po | 3.3 | 3.2 | 4.1 | 0 | 0 | N/A |
| Compound III 100 mg/kg + vemurafenib 50 mg/kg | qweekly + bid | po, po | 2.2 | 2.2 | 3.0 | 0 | 0 | N/A |
| Compound II 100 mg/kg + vemurafenib 50 mg/kg | qd + bid | po, po | 2.5 | 2.0 | 2.9 | 0 | 0 | NA |
| Compound II 200 mg/kg + vemurafenib 50 mg/kg | qweekly + bid | po, po | 1.8 | −0.7 | 3.6 | 0 | 0 | N/A |

Tumor Growth Inhibition (TGI) and Assessment of Survival/Increase in Life Span (ILS)

Efficacy data was graphically represented as the mean tumor volume±standard error of the mean (SEM). Tumor volumes of treated groups were presented as percentages of tumor volumes of the control groups (% T/C), using the formula: $100 \times ((T-T_0)/(C-C_0))$, where T represented mean tumor volume of a treated group on a specific day during the experiment, $T_0$ represented mean tumor volume of the same treated group on the first day of treatment; C represented mean tumor volume of a control group on the specific day during the experiment, and $C_0$ represented mean tumor volume of the same treated group on the first day of treatment.

Prism, version 5.03). An individual tumor volume of 1500 mm$^3$ was used as a surrogate for death. The % ILS was calculated as $100 \times$ [(median survival day of treated group−median survival day of control group)/median survival day of control group]. Median survival was determined utilizing Kaplan Meier survival analysis. Survival in treated groups was compared with the vehicle group by Log-rank (Mantel-Cox) Test (GraphPad Prism, version 4.3, La Jolla, Calif.). Differences between groups were considered significant when the probability value (p) was ≤0.05.

The efficacy results are shown Tables 2, 3 and 4 and FIG. 1.

TABLE 2

Tumor Growth Inhibition

| Group | Frequency | Route | Mean Tumor Volume (mm³) Start Study DAY: 14 | SEM | SD | Mean Tumor Volume (mm³) End Study DAY: 29 | SD | SEM |
|---|---|---|---|---|---|---|---|---|
| Vehicle control | qd + bid | po, po | 141.56 | ±4.56 | ±14.43 | 1749.93 | ±276.89 | ±87.56 |
| Compound III 80 mg/kg | qdx5 | po | 143.00 | ±3.91 | ±12.37 | 705.24 | ±248.91 | ±78.71 |
| Compound III 100 mg/kg | qweekly | po | 147.78 | ±2.13 | ±8.73 | 952.64 | ±474.65 | ±150.10 |
| Compound II 100 mg/kg | qd | po | 146.39 | ±3.01 | ±9.52 | 726.30 | ±300.32 | ±100.11 |
| Compound II 200 mg/kg | qweekly | po | 141.33 | ±3.50 | ±11.06 | 1466.93 | ±359.75 | ±113.76 |
| vemurafenib 50 mg/kg | bid | po | 142.50 | ±3.52 | ±11.12 | 1643.76 | ±347.27 | ±109.82 |
| Compound III 80 mg/kg + vemurafenib 50 mg/kg | qdx5, bid | po, po | 146.39 | ±4.28 | ±13.53 | 400.67 | ±243.95 | ±77.14 |
| Compound III 100 mg/kg + vemurafenib 50 mg/kg | qweekly + bid | po, po | 144.86 | ±2.61 | ±8.25 | 524.26 | ±237.10 | ±74.98 |
| Compound II 100 mg/kg + vemurafenib 50 mg/kg | qd + bid | po, po | 143.48 | ±4.12 | ±13.04 | 550.22 | ±383.07 | ±121.14 |
| Compound II 200 mg/kg + vemurafenib 50 mg/kg | qweekly + bid | po, po | 142.43 | ±2.80 | ±8.85 | 737.79 | ±370.60 | ±117.19 |

TABLE 3

Tumor Growth Inhibition

| Group | % T/C end of study Day: 28 | % Inhibition end of study Day: 28 | p value End of study Day: 28 | Average % Regression per Group | Partial Regression | Full Regression | Animals per Group | % Increased Life Span | p value for % ILS |
|---|---|---|---|---|---|---|---|---|---|
| Vehicle Control | — | — | — | — | 0 | 0 | 10 | — | — |
| Compound III 80 mg/kg | 35 | 65 | <0.001 | — | 0 | 0 | 10 | 29 | <0.0001 |
| Compound III 100 mg/kg | 50 | 50 | <0.001 | — | 0 | 0 | 10 | 29 | 0.001 |
| Compound II 100 mg/kg | 36 | 64 | <0.001 | — | 0 | 0 | 9 | 29 | <0.0001 |
| Compound II 200 mg/kg | 82 | 18 | 0.085 | — | 0 | 0 | 10 | 0 | 0.247 |
| vemurafenib 50 mg/kg | 93 | 7 | 0.453 | — | 0 | 0 | 10 | 0 | 0.342 |
| Compound III 80 mg/kg + vemurafenib 50 mg/kg | 16 | 84 | <0.001 | 0 | 1 | 0 | 10 | 46 | <0.0001 |
| Compound III 100 mg/kg + vemurafenib 50 mg/kg | 24 | 76 | <0.001 | — | 0 | 0 | 10 | 46 | <0.0001 |
| Compound II 100 mg/kg + vemurafenib 50 mg/kg | 25 | 75 | 0.001 | — | 0 | 0 | 10 | 38 | 0.001 |
| Compound II 200 mg/kg + vemurafenib 50 mg/kg | 37 | 83 | 0.001 | — | 0 | 0 | 10 | 29 | 0.0001 |

Assessment of Survival

The relative increased life span (ILS) of the various schedules is shown in Table 4 below. The groups receiving Compound III at 80 mg/kg daily×5 and 100 mg/kg weekly plus vemurafenib 50 mg/kg bid had the greatest percent increase in life span followed by the group receiving Compound II at 100 mg/kg daily plus vemurafenib 50 mg/kg bid.

TABLE 4

Survival Summary

| Group | ILS Calculations | | | |
|---|---|---|---|---|
| | 50% Treatment Days | 50% Vehicle Days | % ILS | p value |
| Vehicle Control | — | — | — | — |
| Compound III 80 mg/kg | 31 | 24 | 29 | <0.0001 |
| Compound III 100 mg/kg | 31 | 24 | 29 | 0.0014 |
| Compound II 100 mg/kg | 31 | 24 | 29 | <0.0001 |
| Compound II 200 mg/kg | 24 | 24 | 0 | 0.2472 |
| vemurafenib 50 mg/kg | 24 | 24 | 0 | 0.3415 |

TABLE 4-continued

Survival Summary

| Group | ILS Calculations | | | |
|---|---|---|---|---|
| | 50% Treatment Days | 50% Vehicle Days | % ILS | p value |
| Compound III 80 mg/kg + vemurafenib 50 mg/kg | 35 | 24 | 46 | <0.0001 |
| Compound III 100 mg/kg + vemurafenib 50 mg/kg | 35 | 24 | 46 | <0.0001 |
| Compound II 100 mg/kg + vemurafenib 50 mg/kg | 33 | 24 | 38 | <0.0001 |
| Compound II 200 mg/kg + vemurafenib 50 mg/kg | 31 | 24 | 29 | <0.0001 |

Statistical Analysis

Statistical cross comparisons are shown in Table 5 below. As shown, the TGI and ILS for the combinations of 100 mg/kg Compound III qweekly+vemurafenib 50 mg/kg bid and 200 mg/kg Compound II qweekly+vemurafenib 50 mg/kg bid were statistically superior to that of all monotherapy arms ($p<0.05$).

TABLE 5

Statistical Comparison Between Groups

| Treatment | versus | Treatment | TGI p value* | ILS p value** |
|---|---|---|---|---|
| Compound III 80 mg/kg qdx5 + vemurafenib 50 mg/kg | | Compound III 80 mg/kg qdx5 | <0.05 | <0.0085 |
| Compound III 80 mg/kg qdx5 + vemurafenib 50 mg/kg | | vemurafenib 50 mg/kg bid | <0.05 | <0.0001 |
| Compound III 100 mg/kg qweekly + vemurafenib 50 mg/kg bid | | Compound III 100 mg/kg qweekly | <0.05 | 0.0021 |
| Compound III 100 mg/kg qweekly + vemurafenib 50 mg/kg bid | | vemurafenib 50 mg/kg bid | <0.05 | <0.0001 |
| Compound II 100 mg/kg qd + vemurafenib 50 mg/kg bid | | Compound II 100 mg/kg qd | <0.05 | <0.3629 |
| Compound II 100 mg/kg qd + vemurafenib 50 mg/kg bid | | vemurafenib 50 mg/kg bid | <0.05 | <0.0001 |
| Compound II 200 mg/kg qweekly + vemurafenib 50 mg/kg bid | | Compound II 200 mg/kg qweekly | <0.05 | 0.0005 |
| Compound II 200 mg/kg qweekly + vemurafenib 50 mg/kg bid | | vemurafenib 50 mg/kg bid | <0.05 | 0.0001 |
| Compound III 80 mg/kg qdx5 + vemurafenib 50 mg/kg bid | | Compound III 100 mg/kg qweekly + vemurafenib 50 mg/kg bid | >0.05 | 0.3774 |
| Compound III 80 mg/kg qdx5 + vemurafenib 50 mg/kg bid | | Compound II 100 mg/kg qd + vemurafenib 50 mg/kg bid | >0.05 | 0.2282 |
| Compound III 80 mg/kg qdx5 + vemurafenib 50 mg/kg bid | | Compound II 200 mg/kg qweekly + vemurafenib 50 mg/kg bid | >0.05 | 0.0013 |
| Compound III 100 mg/kg qweekly + vemurafenib 50 mg/kg bid | | Compound II 100 mg/kg qd + vemurafenib 50 mg/kg bid | >0.05 | 0.6401 |
| Compound III 100 mg/kg qweekly + vemurafenib 50 mg/kg bid | | Compound II 200 mg/kg qweekly + vemurafenib 50 mg/kg bid | >0.05 | 0.0038 |
| Compound II 100 mg/kg qd + vemurafenib 50 mg/kg bid | | Compound II 200 mg/kg qweekly + vemurafenib 50 mg/kg bid | >0.05 | 0.0873 |

*One-Way ANOVA, post-hoc Bonferroni
**Log Rank Test

The invention claimed is:

1. A method of treating a patient suffering from cancer, comprising administering to the patient, either concomitantly or sequentially: (i) a first component comprising vemurafenib or a pharmaceutically-acceptable salt thereof, and (ii) a second component comprising Compound II:

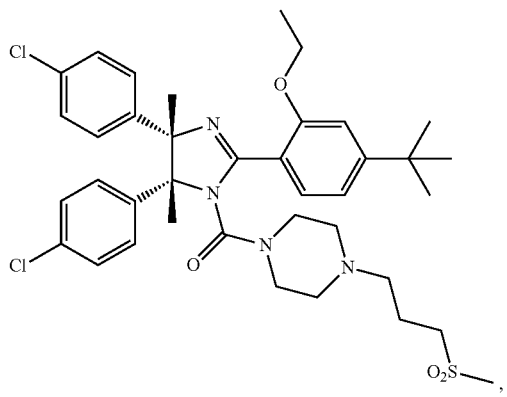 [SMILES: CCOc1cc(C(C)(C)C)ccc1C1=N[C@@](C)(c2ccc(Cl)cc2)[C@@](C)(c2ccc(Cl)cc2)N1C(=O)N1CCN(CCCS(C)(=O)=O)CC1]

or Compound III:

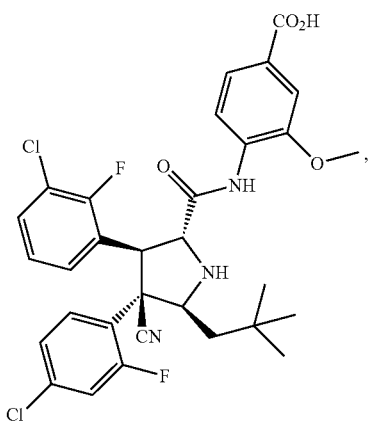 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

or a pharmaceutically-acceptable salt thereof;
the amount of the first and second components being such that the combination thereof is therapeutically effective in the treatment of said cancer;
wherein the cancer is sarcoma, thyroid cancer, or leukemia, and comprises b-Raf having the V600E mutation.

2. The method of claim 1 wherein said cancer is selected from the group consisting of sarcoma and thyroid cancer.

3. The method of claim 1 wherein said cancer is leukemia.

4. The method of claim 1 wherein the patient is a human patient and vemurafenib, or a pharmaceutically-acceptable salt thereof, is administered in an amount of from about 200 mg/day to about 3000 mg/day.

5. The method of claim 4 wherein vemurafenib, or a pharmaceutically-acceptable salt thereof, is administered in an amount of from about 960 mg/day to about 2000 mg/day.

6. The method of claim 1 wherein the patient is a human patient, and the second component comprises Compound II, or a pharmaceutically-acceptable salt thereof, which is administered in an amount of from about 100 mg/day to about 4500 mg/day.

7. The method of claim 6 wherein Compound II, or a pharmaceutically-acceptable salt thereof, is administered in an amount of from about 500 mg/day to about 3500 mg/day.

8. The method of claim 1 wherein the patient is a human patient and the second component comprises Compound III, or a pharmaceutically-acceptable salt thereof, which is administered in an amount of from about 100 mg/day to about 2500 mg/day.

9. The method of claim 8 wherein Compound III, or pharmaceutically-acceptable salt thereof, is administered in an amount of from about 300 mg/day to about 2000 mg/day.

10. The method of claim 6 wherein vemurafenib, or a pharmaceutically-acceptable salt thereof, is administered in an amount from about 480 mg to about 960 mg bid daily on about day 1 through about day 28 of a 28 day cycle, and Compound II, or a pharmaceutically-acceptable salt thereof, is administered once daily in an amount of about 3500 mg/day for about for up to about 5 days on days 1-5 of a 28 day cycle.

11. The method of claim 6 wherein vemurafenib, or a pharmaceutically-acceptable salt thereof, is administered in an amount from about 480 mg to about 960 mg bid daily on about day 1 through about day 28 of a 28 day cycle, and Compound II, or a pharmaceutically-acceptable salt thereof, is administered in an amount about 1500 mg BID for up to about 10 days on days 1-10 of a 28 day cycle.

12. The method of claim 6 wherein vemurafenib, or a pharmaceutically-acceptable salt thereof, is administered in an amount from about 480 mg to about 960 mg bid daily on about day 1 through about day 28 of a 28 day cycle, and Compound II, or a pharmaceutically-acceptable salt thereof, is administered in an amount of about 4500 mg/day on days 1, 8 and 15 of a 28 day cycle.

13. The method of claim 8, wherein vemurafenib, or a pharmaceutically-acceptable salt thereof, is administered in an amount from about 480 mg to about 960 mg bid daily on about day 1 through about day 28 of a 28 day cycle, and Compound III, or a pharmaceutically-acceptable salt thereof, is administered once daily in an amount from 300 mg/day to about 2000 mg/day for about for up to about 5 days on days 1-5 of a 28 day cycle.

14. The method of claim 8, wherein vemurafenib, or a pharmaceutically-acceptable salt thereof, is administered in an amount from about 480 mg to about 960 mg bid daily from about day 1 through about day 28 of a 28 day cycle, and Compound III, or a pharmaceutically-acceptable salt thereof, is administered once weekly in an amount of about 2500 mg/day on days 1, 8 and 15 of a 28 day cycle.

15. The method of claim 1, wherein the cancer is resistant to vemurafenib prior to administration of the first and second components.

* * * * *